United States Patent
Saxena et al.

(10) Patent No.: US 8,263,111 B2
(45) Date of Patent: *Sep. 11, 2012

(54) NON-HORMONAL VAGINAL CONTRACEPTIVE

(76) Inventors: Brij Saxena, Englewood, NJ (US); Mukul Singh, Teaneck, NJ (US); Sidney Lerner, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,858

(22) Filed: Dec. 23, 2011

(65) Prior Publication Data

US 2012/0093910 A1     Apr. 19, 2012

Related U.S. Application Data

(63) Continuation of application No. 12/417,963, filed on Apr. 3, 2009, which is a continuation of application No. 10/362,068, filed as application No. PCT/US01/26475 on Aug. 24, 2001, now Pat. No. 7,521,064.

(60) Provisional application No. 60/227,740, filed on Aug. 24, 2000.

(51) Int. Cl.
  *A61K 3/00* (2006.01)
  *A61K 6/06* (2006.01)

(52) U.S. Cl. .......... 424/430; 424/422; 424/433
(58) Field of Classification Search ................ None
  See application file for complete search history.

(56) References Cited

U.S. PATENT DOCUMENTS

| 3,977,404 | A | * | 8/1976 | Theeuwes | 424/427 |
| 4,959,216 | A | * | 9/1990 | Daunter | 424/430 |
| 5,224,493 | A | * | 7/1993 | Sawan et al. | 128/832 |
| 5,804,191 | A | * | 9/1998 | Scofield | 424/193.1 |
| 6,939,569 | B1 | * | 9/2005 | Green et al. | 424/667 |

FOREIGN PATENT DOCUMENTS

WO      WO02515832 A1 *  2/2002

* cited by examiner

*Primary Examiner* — Susan Tran
(74) *Attorney, Agent, or Firm* — Stroock & Stroock & Lavan LLP

(57) ABSTRACT

The present invention relates to a non-hormonal, biocompatible, and biodegradable intravaginal device for the delivery of spermiostatic, spermicidal and anti-infectious agents. The present invention also relates to methods of contraception using such a device, as well as the prevention and treatment of sexually transmitted diseases and vaginal infections through the application of the device.

17 Claims, 12 Drawing Sheets

A

B

C

NON-HORMONAL VAGINAL CONTRACEPTIVE

CROSS REFERENCE TO RELATED APPLICATIONS

This application is a continuation of currently pending U.S. patent application Ser. No. 12/417,963 filed Apr. 3, 2009, which is continuation of U.S. patent application Ser. No. 10/362,068, filed on Jul. 31, 2003, which is now U.S. Pat. No. 7,521,064 issued on Apr. 21, 2009, titled "NON-HORMONAL VAGINAL CONTRACEPTIVE," which is a National Stage filing of International Application No. PCT/US01/26475 filed Aug. 24, 2001, which claims the benefit of U.S. Provisional Patent Application Ser. No. 60/227,740, filed Aug. 24, 2000, the entire contents of all of which are incorporated herein by reference.

FIELD OF THE INVENTION

The present invention relates to a non-hormonal biodegradable intravaginal device for the delivery of spermiostatic, spermicidal, and anti-infectious agents, and methods for contraception and the prevention and treatment of infection using such a device.

BACKGROUND OF THE INVENTION

Currently, intravaginal barrier and intrauterine contraceptive devices, with or without hormones, are available to inhibit ovulation and to prevent sperm migration into the cervix and fertilization (Roy, "Status of Research and Development of Vaginal Contraceptive Rings as Fertility Control Method in the Female," Research Frontiers in Fertility Regulation, Family Health Network International Bulletin 2(4):1-10 (2000). A literature search for non-hormonal, non-toxic, and non-invasive contraceptive agents, as well as the antimicrobial and anti-viral (U.S. Pat. No. 5,595,980 to Brode) agents revealed that metal ions and their derivatives, such as calcium chloride, sodium chloride, magnesium chloride, copper, and ferrous sulfate act as spermicidal and/or spermiostatic agents (U.S. Pat. No. 4,959,216 to Daunter). Copper sulfate has been used in intrauterine devices ("IUDs") as a spermicidal agent. It is known that sulfhydryl groups are essential components of certain vital enzymes necessary for stability of the sperm. The copper-based agents are toxic due to their sulfhydryl binding properties and thus cause a direct deleterious effect on sperm. Copper also influences midcycle human cervical mucus by causing lysis of the mucus material, changing the physico-chemical properties of the mucus resulting in a decrease in sperm penetration (Shoham et al., "Influence of Different Copper Wires on Human Sperm Penetration Into Bovine Cervical Mucus," In Vitro Contraception 36(3):327-34 (1987)).

Diveley (U.S. Pat. No. 3,950,366) tested metal salts of 1,1,5,5-tetrasubtituted-dithiobiurets as spermiostatic agents. Light metals such as sodium and potassium, alkaline earth metals such as calcium and barium, and heavy metals such as zinc, cadmium, tin, mercury, copper, nickel, chromium, iron, manganese, and cobalt, given orally as chelates, have been shown to form dithiobiuret salts, which act as contraceptive and pregnancy terminators. Sawan et al., (U.S. Pat. No. 5,224,493) showed that insoluble, inorganic metallic salts and oxides of silver, magnesium, zinc, copper, cadmium or arsenic can be used as anti-inflammatory agents. Brode used benzylalkonium chloride, octoxynol-9, nonoxyl-9, ricinoleic acid, and phenol mercury acetates as spermicides delivered via hydrophobically modified polysaccharides as a polymeric delivery system to reduce the potential for infection and sexually transmitted diseases (STD) (U.S. Pat. No. 5,595,980 to Brode).

Cellulose-based vehicles consisting of hydroxyethyl cellulose and hydroxyethyl methyl cellulose, or mixtures thereof, or optionally a cosmetic ingredient selected from the group consisting of water, ethyl alcohol, isopropyl alcohol, glycerin, glycerol, propylene glycol, and sorbitol, have also been used as delivery systems. Typical forms of delivery systems used vaginally include creams, lotions, gels, foams, sponges, suppositories, and films. Daunter used Cu-ethylenediaminetetraac-etic acid/L-ascorbic acid, neuraminidase, and asialofetuin as fertility preventing agents which can be delivered via polyurethane or polyvinyl acetate discs (U.S. Pat. No. 4,959,216 to Daunter). The first two agents act on the cervical mucus to change it from the open cellular structure found at midcycle of the menstrual period to the closed structure that forms an impenetrable barrier for sperm. An ethylene vinyl acetate copolymer has also been used as a component of the matrix for the intravaginal device. Albumin increases the viscosity of the cervical mucus by diminishing the effect on ferning and spinnbarkeit. Albumin, dextran, and vinyl acetate were found to affect mucus spinnbarkeit due to the polymerization of the mucous glycoprotein, resulting in an increase in the viscosity of the cervical mucus. The spermicidal effect of certain devices was also based on their ability to change the vaginal pH to become more acidic (Olmsted et al., "The Rate at Which Human Sperm Are Immobilized and Killed by Mild Acidity," Fertility And Sterility 73(4):687-693 (2000).

The success rate of a contraceptive depends not only upon the efficacy of the contraceptive method, but also upon the user's preference, reversibility, convenience, and compliance. Besides pregnancy, sexual relations can also transmit infection. It is thus beneficial that the design of new contraceptive devices should also consider the option of protecting women against transmission of sexually transmitted diseases (STDs) as well as against pregnancy. Hormone-based contraceptives have long been identified as posing an adverse metabolic risk, and are, in fact, contraindicated for individuals with a variety of cardiovascular conditions. Therefore, new contraceptive devices must be free of toxic compounds and hormones. In addition, a contraceptive method should allow women to use the method themselves in conjunction with normal management of their menstrual cycle as a tampon exchange month after month, thus enhancing the quality of life. However, a controlled release biodegradable delivery vehicle of bioactive agents for contraception over extended periods has not been developed thus far.

There is a pressing need to develop a non-hormonal, biocompatible, non-invasive, cost-effective, biodegradable, and convenient barrier device to prevent pregnancy and infection. The present invention is directed to overcoming these and other deficiencies in the art.

SUMMARY OF THE INVENTION

The present invention relates to a non-hormonal, biocompatible intravaginal device for delivery of spermiostatic and/or spermicidal, and/or anti-infective agents. This device is a flexible structure impregnated with an effective concentration of biocompatible spermiostatic agents and/or spermicidal agents, and/or anti-infective agents.

The present invention also relates to methods of contraception. This method involves introducing a device according the present invention into the vagina of a female mammal.

The present invention also relates to a method of preventing infection in mammals. This method involves introducing the device of the present invention present invention into the vagina of a female mammal.

The present invention also relates to a method of treating vaginal infections in mammals. This method involves introducing the device of the present invention into the vagina of a female mammal.

Contraceptives prevent unwanted pregnancies and provide better family planning and health care. Convenience, safety, efficacy, and cost, as well as the quality of life, are usually the concerns in choosing a contraceptive. The present invention meets these needs by providing a non-hormonal, biodegradable, and biocompatible intravaginal device that acts locally, avoids a systemic route to deliver contraceptive and anti-infection agents, and is easy to use. The flexibility of the device, and the fact that, unlike contraceptive devices such as the cervical cap, the device of the present invention does not need to be carefully positioned, make self-insertion of the device simple. Furthermore, the device of the present invention can be used without detection by a male partner, thus it does not interfere with sexual activity. Despite the fact that the device slowly degrades over the course of efficacy, there is no slippage problem. The device is designed to be inserted by a woman at the very end of her menstrual period, a date which most women are sensitive to and respond to as a matter of course. Thus, usage of the device is not necessarily related to anticipated sexual relations, but rather, to normal post-menstrual hygiene which she attends to ordinarily and regularly. Since both the core and the sheath are composed of biodegradable materials, the device does not need to be removed at the end of its period of effectiveness. Therefore, the delivery device of the present invention allows for a simple, once monthly insertion while providing contraceptive and anti-infective protection for up to 28 days duration.

BRIEF DESCRIPTION OF THE DRAWINGS

FIG. 1A shows the device as a ring with a smooth outer surface. FIG. 1B shows the device as a ring with a highly convoluted outer surface. FIG. 1C shows the device as a ring with a moderately convoluted outer surface.

DETAILED DESCRIPTION OF THE INVENTION

Figure 1:
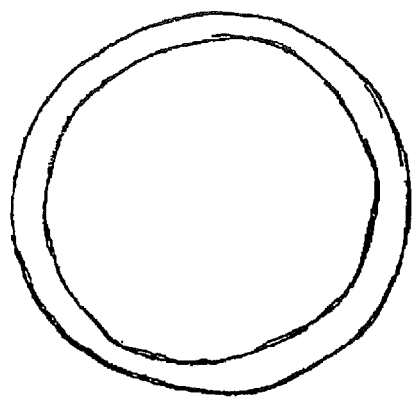
FIGS. 1A-C show some of the physical configurations possible for the device of the present invention.
Figure 1:
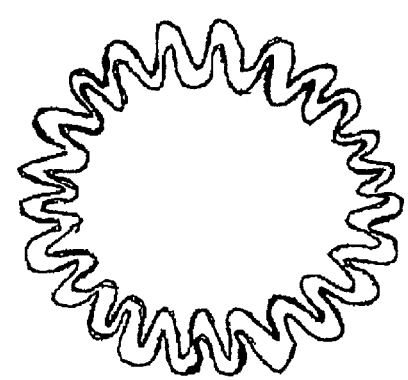
Figure 1:
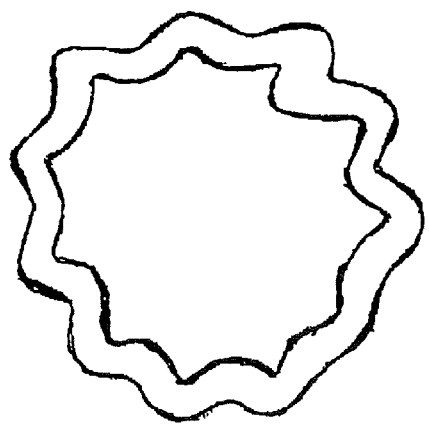

The present invention relates to a non-hormonal biocompatible intravaginal device for delivery of spermiostatic and/or spermicidal, and/or anti-infective agents. This device is a flexible structure, for example, a ring or a modification of a ring, impregnated with an effective concentration of biocompatible spermiostatic agents and/or spermicidal agents, and/or anti-infective agents. Non-hormonal as used herein refers to the use of materials in the device of the present invention which do not include estrogen, progesterone, other steroids, or derivatives thereof, which are systemic in action. In contrast, the materials suitable for the present invention are non-hormonal, non-steroidal, and act locally at the site of insertion. The basic design of the delivery vehicle of the present invention is a hydrogel core-sheath configuration made of biocompatible and biodegradable polymers, which may be either natural and/or synthetic. The objective of the core-sheath configuration is to facilitate the sustained release of impregnated agents for up to a 28-day period. The hydrogel core concept utilizes recent advances in biodegradable three-dimensional hydrogel network biomaterials. Biodegradable hydrogels as a delivery vehicle have the advantage of being environmentally friendly to the human body (due to their biodegradability) and of providing more predictable, controlled release of the impregnated drugs. Hydrogels as delivery vehicles have received significant attention for use as medical implants. Hydrogels are of special interest in biological environments since they have a high water content as is found in body tissue and are highly biocompatible. Hydrogels and natural biological gels have hydrodynamic properties similar to that of cells and tissues. Hydrogels minimize mechanical and frictional irritation to the surrounding tissue because of their soft and compliant nature. Therefore, hydrogels provide a far more user-friendly delivery vehicle than the relatively hydrophobic carriers like silicone, or vinyl acetate.

Recently, two new classes of biodegradable hydrogels have been developed for more controlled release of a wide range of bioactive agents (e.g., indomethacin, doxorubicin, insulin, and albumin) as well as substrates for tissue engineering and regeneration (Kim et al., "Synthesis and Characterization of Dextran-Methacrylate and its Structure Study by SEM," J. Biomed. Mater. Res. 49(4):517 (2000); and Park et al., "Biodegradable Hydrogels for Drug Delivery," Technomic (1993), which are hereby incorporated by reference in their entirety). These new biodegradable hydrogels are synthesized from dextran, a naturally occurring biodegradable, biocompatible, and hydrophilic polysaccharide, and synthetic biodegradable hydrophobic polymers, such as polylactide ("PLA"). Dextran consists primarily of 1,6-.alpha.-D-glucopyranosyl residues and has three hydroxyl groups per glucose residue that could provide greater flexibility in the formulation of hydrogels (Park et al., "Biodegradable Hydrogels for Drug Delivery," Technomic (1993), which is hereby incorporated by reference in its entirety). Dextran has been widely used for many biomedical purposes, such as plasma expander and controlled drug delivery vehicle, because of its highly hydrophilic nature and biocompatibility. It is also possible to incorporate dextranase in order to facilitate biodegradation of dextran for the meeting of specific clinical needs. Both dextran and synthetic biodegradable polyesters like polyglycolide ("PGA"), polylactide ("PLA") or their copolymers are FDA approved raw biomaterials that are commercially successful as synthetic, absorbable polymers for biomedical uses, e.g., as wound closure devices. The degradation products of PGA and PLA are natural metabolites and are readily eliminated by the human body.

The preparation of the dextran/PLA hydrogel core of the present invention is based essentially based on reports and current work by the inventors of the present invention (Kim et al., "Synthesis and Characterization of Dextran-Methacrylate and its Structure Study by SEM," J. Biomed. Mater. Res. 49(4):517 (2000); and Zhang et al., "Synthesis and Characterization of Novel Biodegradable IPN Hydrogels Having Both Hydrophobic and Hydrophilic Components With Controlled Swelling Properties," J. Polymer Chemistry 37:4554-4569 (1999), which are hereby incorporated by reference in their entirety). In brief, the preparation of hydrogel cores involves two major steps. The first step is the incorporation of unsaturated groups onto dextran and PLA, with degree of substitution (DS) used to indicate the level of such incorporation. For example, a higher DS indicates a higher level of unsaturated group incorporation (Kim et al., "Synthesis and Characterization of Dextran-Methacrylate and its Structure Study by SEM," J. Biomed. Mater. Res. 49(4):517 (2000); and Zhang et al., "Synthesis and Characterization of Novel Biodegradable IPN Hydrogels Having Both Hydrophobic and Hydrophilic Components With Controlled Swelling Properties," J. Polymer Chemistry 37:4554-4569 (1999), which are hereby incorporated by reference in their entirety). As described earlier the DS has a profound impact on the rate and extent of diffusion of the incorporated spermiostatic agents out of the hydrogel cores. The purpose of the unsaturated groups is to provide photo-crosslinking capability between dextran and PLA. Materials suitable for use in the present invention include dextran of molecular weight from 43,000 to 70,000 and PLA of molecular weights about 800 to 8,000, which are both readily available from a variety of commercial sources.

Three types of dextran derivatives and one type of PLA derivative are particularly suitable for the core-sheath vehicle of the present invention. Dextran derivatives suitable include, but are not limited to, dextran-maleic acid, dextran allylisocyanate, and dextran-acrylate. In dextran-maleic acid; the unsaturated groups are linked to dextran via ester linkage. In the case of dextran-allyl isocyanate, the linkages between the unsaturated groups and dextran are urethane bonds. Because of the differing sensitivities of the ester linkages (dextran-maleic acid) and urethane linkages (dextran-allyl-isocyanate) toward hydrolytic degradation, different time-dependent swelling of the hydrogel cores for the different types of dextran derivatives used. This provides the ability to control the release rate and the extent of the impregnated spermiostatic agents by controlling the type of dextran precursors. Dextran-maleic acid based hydrogels also have one unique advantage, i.e., the availability of controlled amounts of free —COOH groups which can be used to provide acidity to impede sperm motility as well as sites for further chemical reactions to attach desirable biochemical agents.

The next step for developing dextran-PLA hydrogel cores is the synthesis of PLA diacrylate macromers ("PLAM") which would have the two same unsaturated groups (i.e., acrylate) chemically introduced at the two chains ends of each PLA macromolecule.

The last step of developing hydrogel cores from both dextran derivatives and PLAM precursors involves photo-crosslinking these two precursors in the presence of very small amounts of photoinitiators. In this last step, fixed amounts (5-20% by weight) of a spermiostatic agent, including, but not limited to, the dihydrate form of ferrous gluconate, will be introduced into the precursor solution before crosslinking. Long wavelength UV lamp can be used for photo-crosslinking. The duration of UV exposure can be adjusted to control the level of crosslinking, and hence the swelling and drug release profiles. Optimal concentrations of various spermiostatic agents, as determined for their efficacious release for 3, 7, and 28 days, are incorporated into the newly synthesized biodegradable hydrogel cores.

The sheath material coating the hydrogel core functions to slow down the water penetration into the hydrogel core and to retard the onset of an initial burst release of the agents incorporated into the hydrogel core. Hence, the sheath provides a smooth. i.e., consistent, and sustained release of the impregnated agents. Therefore, synthetic hydrophobic biodegradable polymers like aliphatic polyesters and their copolymers are highly suitable materials for sheath coating. These materials are FDA approved, biocompatible, have a proven record in medicine, have a predictable biodegradation property, are hydrophobic, and are commercially available. Biodegradable aliphatic polyester materials suitable for use as the sheath materials in the present invention include, but are not limited to PLA, poly-.epsilon.-caprolacton-e, polyglycolide, polylactide, co-polymers of polyglycolide, polylactide, and poly-ϵ-caprolactone, and mixtures thereof.

As noted above, a variety of hydrogel cores and sheath materials are suitable for the fabrication of the biodegradable core-sheath matrices of the present invention. By varying the materials as well as architectural parameters, the present invention provides a significantly improved intravaginal contraceptive device that would not only be used easily and comfortably by women, but would also deliver a wide range of spermiostatic and anti-infectious agents with release rates for meeting targeted specific needs. For example, in one aspect of the present invention, the intended use of the device is short term, i.e., a 3 or 7 day contraceptive and/or anti-infective usage. Another aspect of the present invention is a device that provides protection on a monthly basis coincident with a women's menstrual cycle, i.e., for up to 28 days. Thus, the device can be fabricated with more than one hydrogel core, and/or with one or more sheath layers, each comprising a specific combination of the materials described above as needed for the desired application. Examples 7 and 8, below, illustrate the variable design principle of the present invention that permits the present invention to be used for a variety of applications.

Those skilled in the art will appreciate that the newly synthesized hydrogel precursors (i.e., dextran-maleic acid, dextran-ally isocyanate, and PDLAM), hydrogel cores, and the sheath materials are characterized by standard polymer characterizations like FTIR, NMR, elemental analysis, thermal and mechanical analyses, and surface morphology by scanning electron microscope. For the hydrogel cores, additional features like swelling properties, pore size, surface area, and interior morphology are also characterized. Swelling behavior is the most important factor to regulate, as it affects all other essential properties of hydrogels, such as permeability to bioactive agents, biocompatibility, rate of biodegradation, and mechanical properties. Mechanical properties of hydrogels will affect their structural integrity and dimensional stability and will give information about the ability of the hydrogel to resist pressure. The pore size/volume, surface area, and cross-sectional interior morphology allow for the qualitative evaluation of the suitability of pore size and porosity of hydrogels for drug anchorage and release.

Mercury intrusion porosimetery is used to quantify the average pore size, distribution, and pore volume of the hydrogels. BET surface area analysis can be used to determine the surface area of the three dimensional hydrogels. The technical aspects of these characterizations are routine laboratory determinations, and well within the scope and capability of one skilled in the art. The detailed procedures have been described by the inventors, for example in Kim et al., "Synthesis and Characterization of Dextran-Methacrylate and its Structure Study by SEM," J. Biomed. Mater, Res. 49(4):517 (2000); and Zhang et al., "Synthesis and Characterization of Novel Biodegradable IPN Hydrogels Having Both Hydrophobic and Hydrophilic Components With Controlled Swelling Properties," J. Polymer Chemistry 37:4554-4569 (1999), which are hereby incorporated by reference in their entirety.

In one aspect of the present invention the biodegradable core-sheath biomaterials of the present invention will be cast as an intravaginal contraceptive device in the form of a ring, or modification thereof, such as a disc. Rings have been determined to be particularly comfortable for intravaginal application. Other physical structures may also be used. It will be appreciated by those skilled in the art that the shape of the device of the present invention may be adjusted to best accommodate the desired application. In one aspect of the present invention the device has a smooth outer surface, as shown in FIG. 1A. In another aspect of the present invention the device has a convoluted surface, such as those shown in FIGS. 1B and 1C. As noted above, mechanical aspects of the device, such as surface area and interior morphology, will determine hydrogel swelling and, ultimately, the release rate of agents from the impregnated core. Therefore, the outer surface shape of the device can be varied along with the biodegradable materials of the core-sheath, to optimize release rates for a given application of the device.

Another aspect of the present invention is a method of contraception for mammals, including, but not limited to, humans. This involves introducing the biodegradable, biocompatible intravaginal delivery device of the present invention, incorporated with an effective concentration of biocompatible spermiostatic and/or spermicidal agents, into the vagina of a female mammal. Spermiostatic as used herein refers to the ability to completely retard sperm motility. Spermicidal refers to the ability to kill sperm, which may be effected physiologically when sperm have been irreversibly immobilized (Olmsted et al., "The Rate at Which Human Sperm Are Immobilized and Killed by Mild Acidity," Fertility And Sterility 73(4) 687-693 (2000), which is hereby incorporated by reference in its entirety). The spermiostatic/spermicidal aspect of the present invention is a provided by a three-pronged attack. Specific agents are included to: 1) reduce sperm motility to zero; 2) increase the viscosity of cervical mucus to impede the sperm motility; and 3) sustain a pH of approximately 5.0 in the vaginal cavity to augment the total spermiostatic effect. Spermiostatic/spermicidal agents suitable for the present invention include, but are not limited to, magnesium chloride, calcium chloride, ferrous sulfate, copper sulfate, ferrous gluconate, and mixtures thereof. The use of these metallic salts as spermiostatic agents, and concentrations effective for spermiostatic efficacy are known to those skilled in the art (see, for example, U.S. Pat. No. 4,959, 216 to Daunter; and Shoham et al., "Influence of Different Copper Wires on Human Sperm Penetration Into Bovine Cervical Mucus," In Vitro Contraception 36(3):327-34 (1987), which are hereby incorporated by reference in their entirety).

The secretory cells of the mucosa of the cervix produce a secretion called cervical mucus, a mixture of water, glyco-protein, serum-type proteins, lipids, enzymes, and inorganic salts. Females of reproductive age secrete 20-60 ml of cervical mucus per day. Cervical mucus is more receptive to sperm at or near the time of ovulation because it is less viscous, and becomes more alkaline, with a pH of about 7.5-8.5, in the presence of semen. After the ovulation, whether or not sexual relations have occurred, the mucus becomes very thick and forms a cervical plug that is physically impenetrable to sperm. And then the cycle repeats, with the mucus becoming less viscous as ovulation approaches and thicker afterwards.

Therefore, it follows that if viscosity of the cervical mucus were increased during the period of the cycle when it is less viscous, then sperm motility would be impeded. An agent suitable for increasing the viscosity of the cervical mucous in the device of the present invention is L-ascorbic acid. It has been shown that L-ascorbic acid, more commonly known as Vitamin C, is successful in triggering the above-described chain of events. Ascorbic acid can act as a reducing agent on the mucopolysaccharides of the cervical mucus. It transfers electrons to the mucopolysaccharides, causing the cervical mucus to change conformation. The open cellular structure that the mucus cells originally have is subsequently closed, thus causing an increase in viscosity. This increased viscosity results in inhibited sperm motility. The increase in the viscosity of the cervical mucus induced by the release of L-ascorbic acid from the delivery device of the present invention serves as the second line of resistance for the sperm to reach the ovum.

The optimum pH value for sperm migration and sperm survival in the cervical mucus is between 7.5 and 8.5, while acid mucus immobilizes sperm in the vagina, thus preventing contraception (WHO Laboratory Manual for the Examination of Human Semen and Sperm-cervical Mucus Interaction, Ch. 5:51-59 (1999), which is hereby incorporated by reference in its entirety). It appears that the immobilization of sperm that occurs in the vagina at a pH of or about 5.0 may cause the death of the sperm by creating an environment wherein the sperm are irreversibly immobilized (Olmsted et al., "The Rate at Which Human Sperm Are Immobilized and Killed by Mild Acidity," Fertility And Sterility 73(4):687-693 (2000), which is hereby incorporated by reference in its entirety). The device of the present invention functions to sustain the vaginal pH at or about a 5.0 in two ways. First, poly-amino and polycarboxylic acid mixtures (ampholines), with a pH range of 4-6, are incorporated into the biodegradable core-sheath matrix. As these are released, they maintain the vaginal pH in the acidic range (at or about pH 5.0), even in the presence of semen. Secondly, as described in greater detail in Example 4, the biomaterials of the hydrogel core can contribute to an acidic environment as well. When acid-rich matrices contain, for example, maleic acid, they help sustain the vaginal pH around 5.0 as the biomaterial is released into the vagina during the period of efficacy of the device.

One of the prime advantages of this unique three-pronged approach to contraception provided by the present invention is that the combination of methods provides for greater efficacy and dependability than other contraceptive measures which incorporate any one, or even two, of these approaches in a single contraceptive. Further more, because the multiple prongs contribute simultaneously to the immobilization and death of sperm, relatively low concentrations of spermiostatic/spermicidal agents are needed. Furthermore, the non-hormonal, non-systemic, and biodegradable nature of the present invention provides a method of contraception that can be used regularly and long-term without negative repercussions to users' health.

Another aspect of the present invention is a method of preventing infection in mammals including, but not limited to, humans, by introducing the biocompatible, biodegradable device of the present invention in the vagina of a female mammal. This additional advantage can be accomplished by incorporating anti-infectious agents into the device, with or without the spermiostatic agents. Anti-infective agents suitable for the present invention include anti-viral agents, anti-fungal agents, antibiotics, and mixtures thereof. This is includes prophylactic treatment against sexually transmitted diseases ("STDs") such as HIV, particularly for those in high risk populations. Depending on the intended application of the device, the anti-infective agents of the present invention can be used with or without the sperm iostatic and/or spermicidal agents described above.

Another aspect of the present invention is a method of treating vaginal infections in mammals including, but not limited to, humans, by introducing the non-hormonal, biocompatible, biodegradable device of the present invention in the vagina of a female. This involves the incorporation of antibiotics, such as tetracycline, and/or anti-fungal, agents into the device, with or without the addition of spermiostatic or spermicidal agents.

EXAMPLES

Example 1

Efficacy of Various Metal Salts on Sperm Motility

Figure 2:
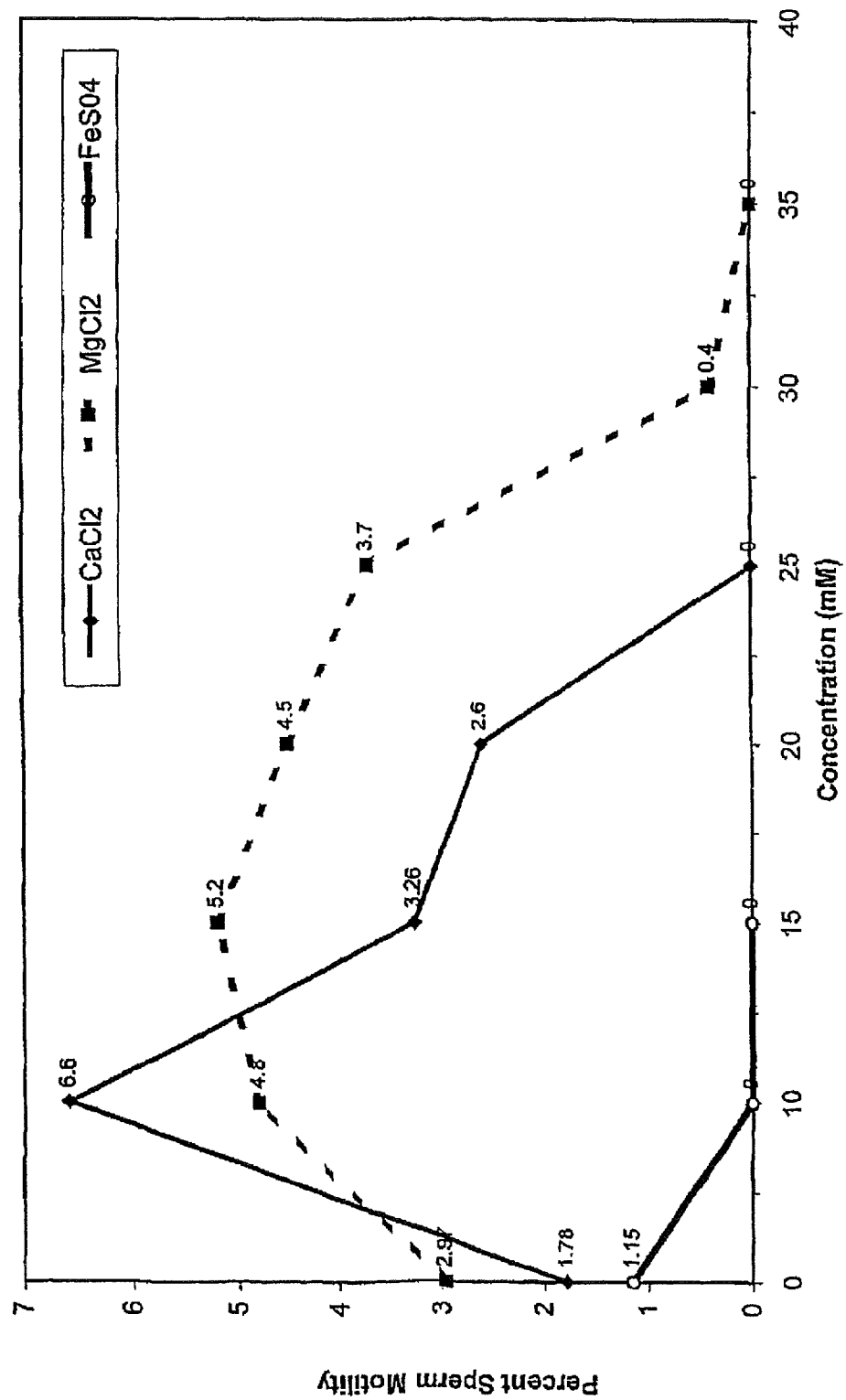
FIG. 2 shows the effects of calcium chloride (CaCl.sub.2), magnesium chloride (MgCl.sub.2), and ferrous sulfate (FeSo.sub.4) on sperm motility.
Figure 3:
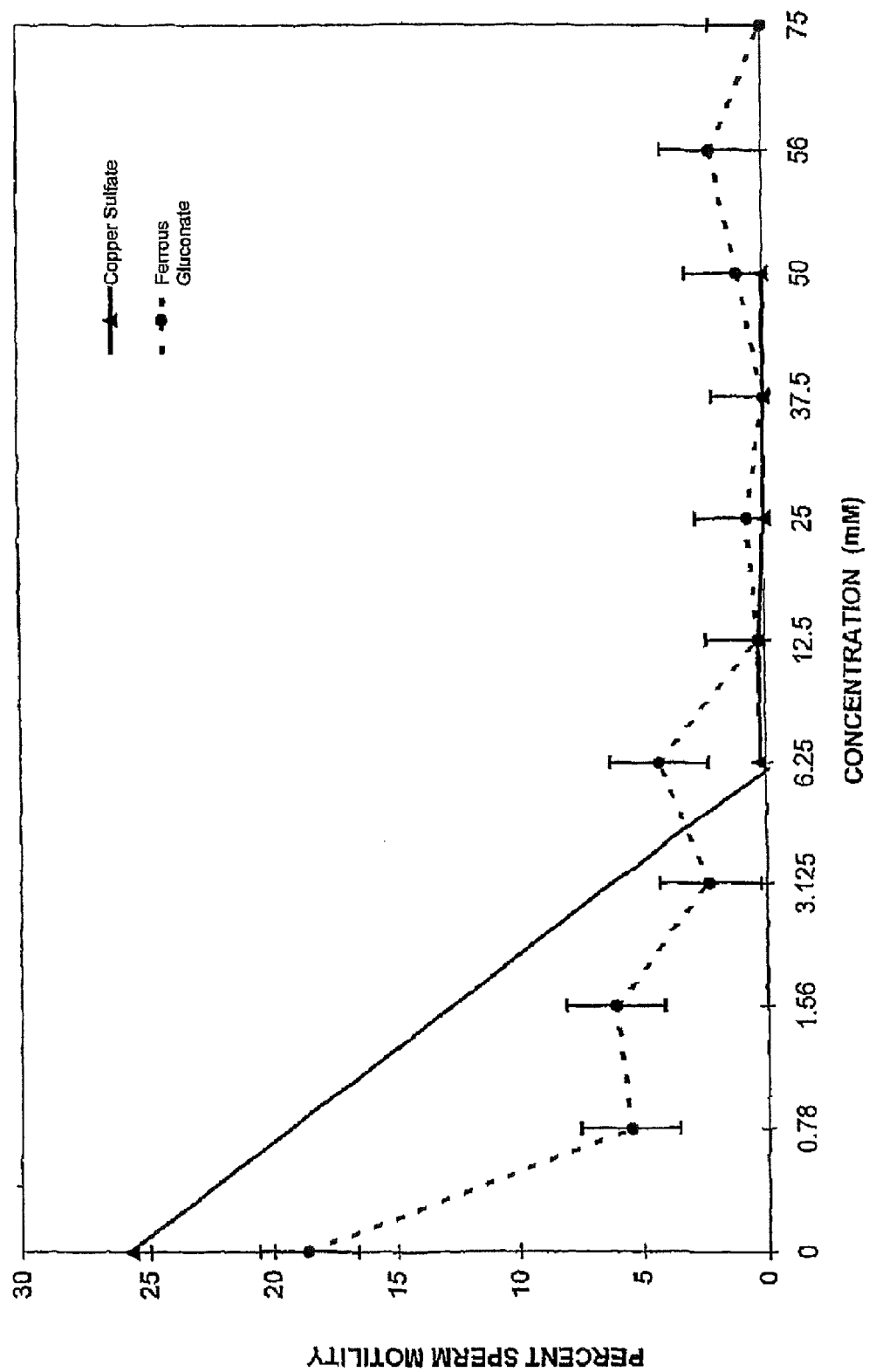
FIG. 3 shows the effects of copper sulfate and dihydrate ferrous gluconate on sperm motility in vitro.
Figure 4:
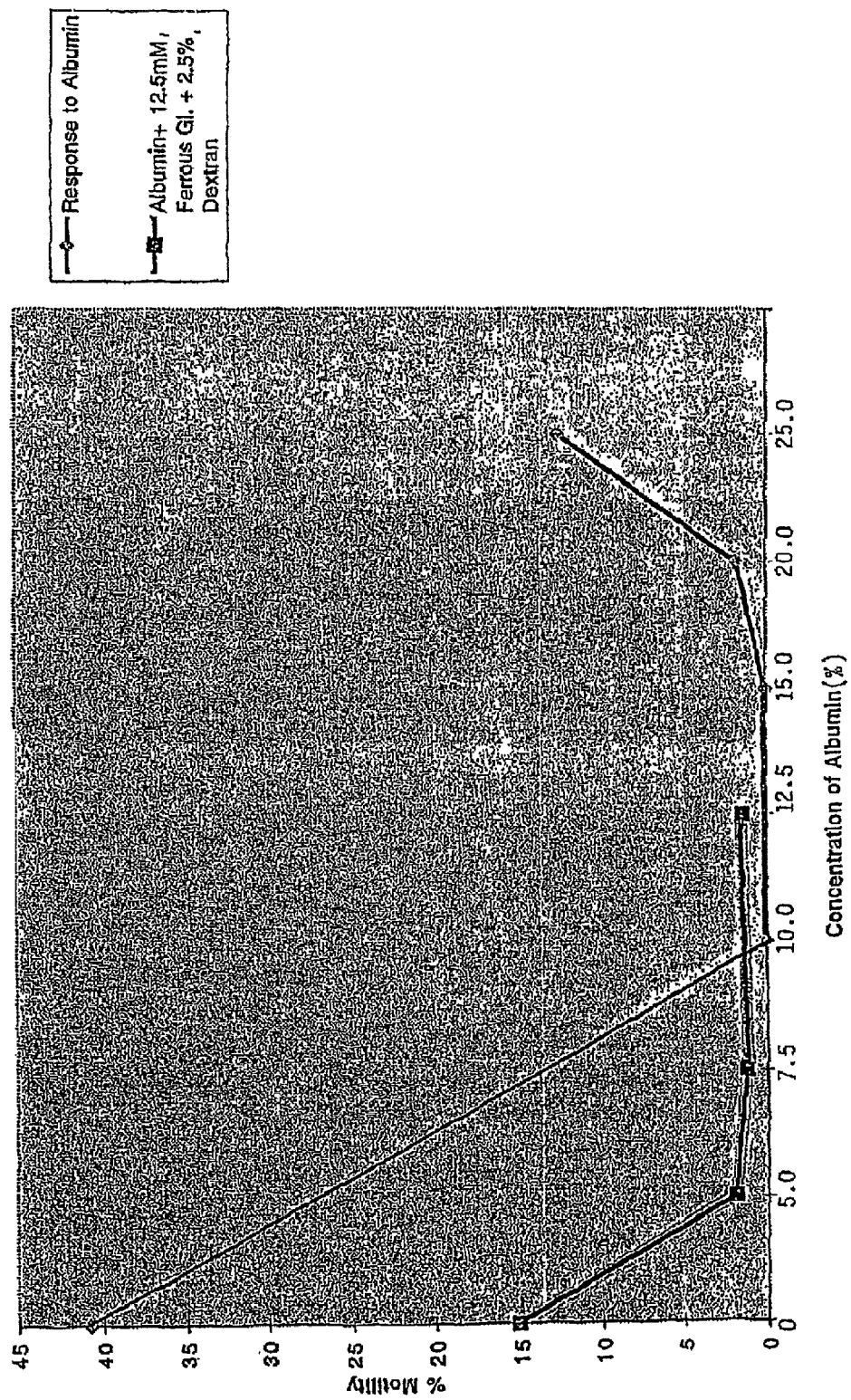
FIG. 4 shows the effects of 12.5 mM ferrous gluconate on sperm motility in the presence of increasing concentration of albumin, with and without 2.5% dextran added.
Figure 5:
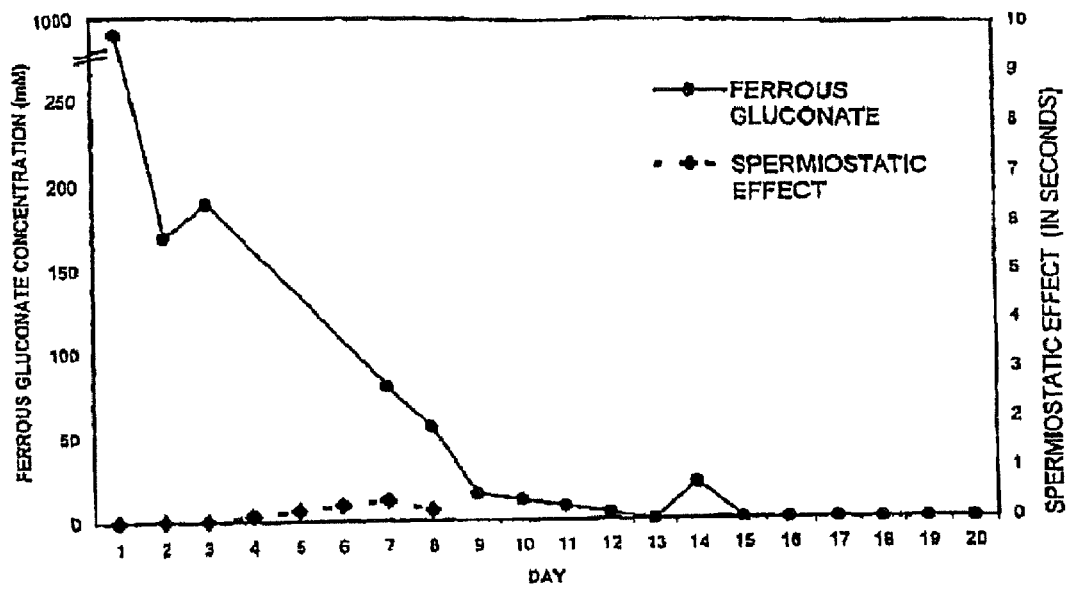
FIG. 5 shows the daily release of ferrous gluconate from matrix Sample A and the spermiostatic effect (in seconds) over a 20 day time course.

The effects of various concentrations of magnesium chloride, calcium chloride, ferrous sulfate, copper sulfate, and ferrous gluconate on the motility of human sperm were studied in vitro. As shown in FIG. 2, calcium chloride ($CaCl_2$) and magnesium chloride ($MgCl_2$) were spermiostatic at concentrations of 25 mM and 35 mM, respectively, whereas ferrous sulfate ($FeSO_4$) completely arrested the motility of human sperm at a concentration of 10 mM. Copper sulfate and ferrous gluconate were spermiostatic at concentrations of 6.25 mM and 12.5 mM, respectively, as shown in FIG. 3. 25 mM solutions of copper sulfate and ferrous gluconate showed 93.3% and 97.4% immobilization of sperm, respectively, as shown in FIG. 3. 37.5 mM solutions of both reagents completely immobilized all the sperm, shown in FIG. 3. However, in the presence of the dihydrate form of ferrous gluconate, the spermiostatic effect was immediate. At lower concentrations of albumin and dextran, the spermiostatic effects were not significant; however, increasing the concentration of albumin to 10% decreased sperm motility almost close to that of 12.5 mM concentration of ferrous gluconate, as shown in FIG. 4. Addition of 2.5% dextran and 5% albumin to 12.5 mM ferrous gluconate showed no enhancement of the spermiostatic effect, as shown in FIG. 4. Similarly, no additional spermiostatic effect was observed when 2.5% dextran was added to a 12.5-mM ferrous gluconate solution or when it was added to a 6.5-mM copper sulfate solution. However, in 20% albumin and 40% albumin almost 97% of the sperm were completely immobilized. In a 1.25% solution of dextran almost 95% of the sperm were immobilized.

On the basis of the above observations, the iron salt in the form of ferrous gluconate, was further evaluated as the spermiostatic agent. Ferrous gluconate is not toxic, is biocompatible, and is used as a nutritional iron supplement. Iron promotes lipid peroxidation. Lipid peroxidation is a type of cellular damage involving the formation of oxygen free radicals, such as super-oxide anion (Hong et al., "Effect of Lipid Peroxidation on Beating Frequency of Human Sperm Tail," Andrologia 26:61-65 (1993); Aitken et al., "Relationship Between Iron-Catalyzed Lipid Peroxidation Potential and Human Sperm Function," J. Reproduction and Fertility 98:257-265 (1993); and Calamer et al., "Effect of Lipid Peroxidation Upon Human Spermatic Adenosinetriphosphate (ATP). Relationship With Motility, Velocity and Linearity of the Spermatozoa," Andrologia 21(1):48-49 (1988), which are hereby incorporated by reference in their entirety). Radicals are extremely unstable and unfavorable to the lipid bilayer of a cell resulting in cell damage. The lipid peroxidation process, as shown below, is initiated in human spermatozoa when intracellular production of reactive oxygen species overwhelms the antioxidant defense system, namely, superoxide dismutase (SOD), used by the cell. Human spermatozoa are enriched with unsaturated fatty acids and fatty acids are particularly susceptible to lipid peroxidation. Sperm are thus predisposed to peroxidative damage. This reaction occurs when lipid peroxides in the bilayer of sperm tails are exposed to ferrous ion resulting in the propagation of lipid peroxidation, which leads to a continuous formation and decomposition of lipid peroxides. Eventually, this causes structural damage, a decline in metabolic activity, and spermiostatic effects in sperm cells. Ferrous gluconate targets sperm tail and causes lipid peroxidation as shown below. 1

Example 2

Effect of Various Concentrations of Ascorbic Acid on the Viscosity of Human Cervical Mucus At the commencement of the menstrual cycle, cervical mucus has a tight honey-comb cellular structure with a channel diameter of 2-6 m.mu.m, which forms an impenetrable barrier to sperm. At midcycle, the channel diameter is 30-35 m.mu.m in order to allow the sperm to pass. At the luteal phase, the cellular structure again contracts to 2-6 m.mu.m, and the mucus becomes more viscous (WHO Laboratory Manual for the Examination of Human Semen and Sperm-cervical Mucus Interaction, Ch. 5:51-59 (1999), which is hereby incorporated by reference in its entirety). L-ascorbic acid is an antioxidant, transfers electrons, and acts as a reducing agent for disulfide (—S—S—) bonds of mucopolysaccharides of glycoproteins forming the cervical mucus, thus changing the mucus from open cellular structure found at midcycle of the menstrual period to the closed cellular structure to form an impenetrable barrier for sperm. The effect on L-ascorbic acid was tested in vivo using cervical samples collected from female volunteers during their fertile phase.

To collect cervical mucus from female volunteers, the cervix is exposed with a speculum, and the external os is gently wiped with a cotton swab to remove the external pool of vaginal contaminants. Cervical mucus is aspirated with a needleless tuberculin syringe. The pH of the collected cervical mucus is determined with pH paper (range 6.4-8.0). The optimum pH value for sperm migration and survival in the cervical mucus is between 7.0 and 8.5. Acidic mucus immobilizes spermatozoa (WHO Laboratory Manual for the Examination of Human Semen and Sperm-cervical Mucus Interaction, Ch. 5:51-59 (1999), which is hereby incorporated by reference in its entirety). Mucus is preserved in the original tuberculin syringe and covered with parafilm to avoid dehydration. The samples are preserved in a refrigerator at 4.degree. C. for a period not exceeding 5 days. Usually the mucus specimens are utilized within 2 days of collection. Various dilutions of L-ascorbic acid are mixed with an appropriate aliquot of mucus and incubated for 30 minutes at 37.degree. C. and the cervical mucus consistency is determined. Cervical mucus consistency is scored as recommended by WHO (WHO Laboratory Manual for the Examination of Human Semen and Sperm-cervical Mucus Interaction, Ch. 5:51-59 (1999), which is hereby incorporated by reference in its entirety) as follows. Various parameters of cervical mucous consistency of untreated and treated mucus can be compared to determine the optimum amount of ascorbic acid needed to achieve desired viscosity of the mucus.

1 Score Viscosity 0=Thick, highly viscous, premenstrual mucus 1=Mucus of intermediate viscosity 2+=Mildly viscous 3=Watery, minimally viscous, mid-cycle (pre-ovulatory mucus)

A second parameter of the cervical mucus examined is known as the spinnbarkeit of the mucus. Spinnbarkeit is the term used to describe the fibrosity, the threadability, or the elasticity of cervical mucus. Cervical mucus placed on a microscope slide is touched with a cover slip, or a second slide held crosswise, which is lifted carefully. The length of the cervical mucus thread stretches in between the two surfaces is estimated in centimeters and scored as follow (WHO Laboratory Manual for the Examination of Human Semen and Sperm-cervical Mucus Interaction, Ch. 5:51-59 (1999), which is hereby incorporated by reference in its entirety):

2 Score Length (in cm.) 0=less than 1 cm 1=1-4 cm 2=5-8 cm 3=9 cm or more

The effect of L-ascorbic acid on ferning was also tested. Ferning refers to the degree and pattern of crystallization of the mucus observed when dried on a glass surface. Ferning is due to decreased levels of salt and water interacting with glycoprotein on the mucus. Ferning is increased in capacity as ovulation approaches. To test for ferning, cervical mucus is laced in a glass slide, air-dried, and viewed under a light microscope. Ferning is scored as follows:

3 Score Description of ferning 0=No crystallization 1=Atypical fern formation 2=Primary and secondary stems, ferning 3=Tertiary and quaternary stems, ferning For the purpose of the present invention, ascorbic acid is oxidized to dehydroascorbic acid and the latter is coupled with 2,4-dinitrophenylhydrazine. The coupling reaction forms the 2,4-dinitrophenylosazone of dehydroascorbic acid, a light-brown crystalline compound. When treated with 85% $H_2SO_4$, the osazone is rearranged to form a reddish colored compound, which absorbs maximally at 500 to 550 nm. It is a highly stable product under the conditions used and is well suited to colorimetric measurement.

Reagents for this include: trichloroacetic acid solutions, 6% and 4%; 2,4-Dinitrophenylhydrazine reagent. A stock solution of ascorbic acid is made by dissolving 50 mg of ascorbic acid of the highest purity in 100 ml of 0.5% oxalic acid. Store at 4.degree. C.

To make a standard solution of dehydroascorbic acid, place 2 ml of the ascorbic acid stock solution in a 100 ml volumetric flask and make up to volume with 4% trichloroacetic acid solution. This solution is oxidized by adding 1 teaspoonful or (1 g) of acid-washed Norite per 50 ml, shaking thoroughly, and filtering through Whatman No. 42 filter paper. One ml of this solution contains 10 .mu.g of dehydroascorbic acid. Store at 4.degree. C.

To prepare solution filtrate: to one volume of solution, add 19 volumes of 4.0% trichloroacetic acid. This dilution will serve for a range of 1 to 300 mg of ascorbic acid per liter of solution.

The procedure is as follows. Place 4 ml of Norite filtrate of unknowns in each of two matched photoelectric calorimeter tubes. Place in another matched colorimeter tube 4 ml of the dehydroascorbic acid standard solution (10 .mu.g per ml). To the standard tube and the tube containing Norite filtrate, add 1 ml of 2,4-dinitrophenylhydrazine reagent. The other tube containing Norite filtrate is used as a control, no reagent being added to the tube at this time. Place the three tubes in a constant temperature water bath at 37.degree. C. Keep the tubes immersed in the bath for exactly 3 hours. Remove and place them in a beaker of ice water containing generous quantities of ice. To each of the three tubes, while in the ice water bath, add slowly 5.0 ml of 85% $H_2SO_4$. Finally, to the control tubes, add 1 ml 2,4-dinitrophenylhydrazine reagent. The tubes are shaken under the ice water to achieve complete mixing and are then placed in a rack. After 30 minutes, wipe the tubes dry and clean and record the absorption in a calorimeter using, a 540 m.mu. filter. To take the reading, use the control tube to set the colorimeter at 100% transmittance or zero absorbance (Roe, in Seligson, ed., Standard Methods of Clinical Chemistry, Vol. 3, New York: Academia Press, p. 35 (1961), which is hereby incorporated by reference in its entirety). The cervical mucous scores from four samples tested at concentrations of ascorbic acid from 0-10% are shown below in Table 1.

TABLE 1

CERVICAL MUCUS SCORES AT VARIOUS CONCENTRATIONS OF ASCORBIC ACID FOR FOUR DIFFERENT SAMPLES

|  | 0% | 0.31% | 0.63% | 1% | 1.25% | 2.50% | 5% | 10% |
|---|---|---|---|---|---|---|---|---|
| Jun. 22, 2000 | | | | | | | | |
| pH | 4 ± .71 | 5 ± .9 | 4 ± .9 | 4 ± .53 | 3 ± .38 | 3 ± .58 | 3 ± .75 | 2 ± 1.13 |
| Quantity | .3 ± .53 | .3 ± .67 | .3 ± .67 | .3 ± .67 | .3 ± .67 | .3 ± .67 | .3 ± .67 | .3 ± .67 |
| Viscosity | 0 | 3 ± .79 | 1 ± .81 | 1 ± .75 | 1 ± .95 | 2 ± .61 | 2 ± .52 | 1 ± .69 |
| Ferning | 3 ± .38 | 2 ± .86 | 0 ± | 2 ± .82 | 0 | 0 | 0 | 1 ± .53 |
| Spinnbarkeit | 1 ± .79 | 0 | 1 ± .49 | 1 ± .51 | 1 ± .51 | 1 ± .14 | 1 ± .35 | 1 ± .26 |
| Cellularity | 3 ± .38 | 2 ± .86 | 0 | 2 ± .82 | 0 | 0 | 0 | 1 ± .53 |
| TOTAL | 7.3 | 7.3 | 2.3 | 6.3 | 2.3 | 3.3 | 3.3 | 4.3 |
| Jun. 23, 2000 | | | | | | | | |
| pH | 8 ± .71 | 2 ± .9 | 2 ± .9 | 3 ± .53 | 3 ± .38 | 3 ± .58 | 3 ± .75 | 2 ± 1.13 |
| Quantity | .2 ± .53 | .2 ± .067 | .2 ± .067 | .2 ± .067 | .2 ± .067 | .2 ± .067 | .2 ± .067 | .2 ± .067 |
| Viscosity | 2 ± 1 | 3 ± .79 | 2 ± .81 | 2 ± .75 | 3 ± .95 | 0 | 2 ± .52 | 2 ± .69 |
| Ferning | 3 ± .38 | 0 | 0 | 0 | ± | 0 | 0 | 1 ± .53 |
| Spinnbarkeit | 2 ± .79 | 1 ± .35 | 1 ± .49 | 1 ± .51 | 1 ± .51 | 1 ± .14 | 0 | 1 ± .26 |
| Cellularity | 2 ± .68 | 2 ± .58 | 0 | 0 | 0 | 1 ± .49 | 0 | 1 ± .51 |
| TOTAL | 9.2 | 6.2 | 3.2 | 3.2 | 4.2 | 2.2 | 2.2 | 5.2 |
| pH | 4 ± .71 | 4 ± .9 | 4 ± .9 | 4 ± .53 | 4 ± .38 | 2 ± .58 | 2 ± .75 | 2 ± 1.13 |
| Quantity | .15 ± .53 | .15 ± .067 | .15 ± .067 | .15 ± .067 | .15 ± .067 | .15 ± .067 | .15 ± .067 | .15 ± .067 |
| Viscosity | 0 | 2 ± .79 | 1 ± .81 | 2 ± .75 | 1 ± .95 | 1 ± .61 | 2 ± .25 | 1 ± .69 |
| Ferning | 3 ± .38 | 0 | 0 | 0 | 0 | 0 | 0 | 0 |

TABLE 1-continued

CERVICAL MUCUS SCORES AT VARIOUS CONCENTRATIONS
OF ASCORBIC ACID FOR FOUR DIFFERENT SAMPLES

|  | 0% | 0.31% | 0.63% | 1% | 1.25% | 2.50% | 5% | 10% |
|---|---|---|---|---|---|---|---|---|
| Spinnbarkeit | 1 ± .79 | 0 | 1 ± .49 | 1 ± .51 | 0 |  | 1 ± .35 | 1 ± .26 |
| Cellularity | 3 ± .68 | 1 ± .58 | 1 ± .61 | 0 | 1 ± .53 | 1 ± .49 | 0 | 1 ± .51 |
| TOTAL | 7 | 3.15 | 3.15 | 3.15 | 2.15 | 2.15 | 2.15 | 3.15 |
| pH | 7 ± .71 | 4 ± .9 | 5 ± .9 | 4 ± .53 | 4 ± .38 | 4 ± .58 | 2 ± .75 | 3 ± 1.13 |
| Quantity | 0.2 ± .53 | .2 ± .067 | .2 ± .067 | .2 ± .067 | .2 ± .067 | .2 ± .067 | .2 ± 0.67 | .2 ± .067 |
| Viscosity | 3 ± 1 | 2 ± .79 | 3 ± .81 | 2 ± .75 | 3 ± .95 | 2 ± .61 | 2 ± .52 | 0 |
| Ferning | 3 ± .38 | 0 | 3 ± .86 | 3 ± .82 | 2 ± 1.13 | 1 ± .82 | 0 | 0 |
| Spinnbarkeit | 3 ± .79 | 1 ± .35 | 1 ± .49 | 1 ± .51 | 1 ± .51 | 1 ± .14 | 1 ± .35 | 0 |
| Cellularity | 2 ± .68 | 0 | 0 | 0 | 1 ± .53 | 1 ± .49 | 1 ± .66 | 0 |
| TOTAL | 11.2 | 3.2 | 7.2 | 6.2 | 7.2 | 5.2 | 4.2 | 0.2 |

*pH NOT INCLUDED IN TOTAL

It is evident from the cervical mucus score that overall viscosity of the mucus increased in direct relationship with increasing concentrations of L-ascorbic acid from 0.31% to a range of 1-2.5%. As shown in Table 2, the daily eluates for twelve consecutive days of hydrogel matrix DA containing L-ascorbic acid also increased the viscosity of the cervical mucus equivalent to that of normal follicular and luteal phases.

TABLE 2

CERVICAL MUCUS SCORE OF THE DAILY ELUATES OF THE MATRIX

| Parameter | May 10, 2000 | May 11, 2000 | May 12, 2000 | May 13, 2000 | May 14, 2000 | May 15, 2000 | May 16, 2000 | May 17, 2000 | May 18, 2000 | May 19, 2000 | May 20, 2000 | May 21, 2000 |
|---|---|---|---|---|---|---|---|---|---|---|---|---|
| pH | 7 | 7 | 7 | 7 | 7 | 5 | 7 | 3 | 4 | 5 | 4 | 6 |
| Viscosity | 0 | 0 | 0 | 1 | 1 | 0 | 0 | 1 | 0 | 1 | 2 | 2 |
| Ferning | 1 | 0 | 0 | 2 | 2 | 0 | 0 | 0 | 0 | 0 | 0 | 0 |
| Spinnbarkeit | 0 | 0 | 1 | 1 | 0 | 0 | 1 | 1 | 0 | 1 | 1 | 1 |
| Cellularity | 2 | 2 | 2 | 2 | 2 | 0 | 0 | 0 | 0 | 0 | 0 | 0 |
| TOTAL | 3 | 2 | 3 | 6 | 5 | 0 | 1 | 2 | 0 | 2 | 3 | 3 |

Normal Average values (number of subjects) of the total cervical mucus score (Viscosity, Ferning, Spinnbarkeit and Cellularity)
Follicular Phase 3.6 (11)
Midcycle 13.1 (3)
Luteal Phase 4.4 (6)

Example 3

Three Generations of Biodegradable Matrices and their Controlled Release of Ferrous Gluconate Three generations of biodegradable matrices impregnated with dihydrate ferrous gluconate were designed and tested for release profiles and efficacy on sperm motility.

The first generation matrix tested consisted of an aliphatic polyester copolymer from PLA and poly (F-caprolactone) containing 24% ferrous gluconate by weight. Aliphatic polyesters have a proven record in the biomedical field, predictable biodegradation properties, FDA approval, and commercial availability. The first generation matrix was the simplest design for determining whether the concept of controlled release of spermiostatic agents from biodegradable substrates would be feasible and warrant additional studies.

The release data from the first generation matrix prompted the development of a sandwich design, which was used for the second generation matrix. The purpose of this sandwich configuration was to enhance the controlled release of the impregnated spermiostatic agent, particularly after the initial release. The center layer of the sandwich was a copolymer of PLA and Poly(.epsilon.-caprolactone) containing 38.7% of ferrous gluconate. The top and bottom layers were poly(.epsilon.-caprolactone) homopolymer ("PCL") containing 21.5% ferrous gluconate by weight.

Since the release of ferrous gluconate from the 1st and 2nd generation biodegradable matrices showed a relatively short lived 24 hour burst release profile and the matrices did not have sufficient ferrous gluconate remaining as the reservoir for subsequent sustained spermiostatic activity, a third generation biodegradable matrix was designed. This third generation biodegradable matrix employed a new biodegradable core and sheath design concept to provide more sustained and smooth release over a long period. The hydrogel gel was based on a new technology (Park et al., "Biodegradable Hydrogels for Drug Delivery," Technomic (1993), which is hereby incorporated by reference in its entirety). This inner hydrogel core was covered by biodegradable sheath. The objective of the hydrogel core is to provide sustained release of the contraceptive agents during the late stage as well as to compensate for the declining concentration of the agents released from the sheath materials in the early stage. The intended functions of the sheath materials are three fold. First, they would retard the onset of swelling of the hydrogel core during the early stage of application and hence preserve its impregnated contraceptive agents for later stage release. Second, the sheath materials could also restrict the well-known burst release of drugs from the hydrogel core so that it would "smooth out" the release of the incorporated agents from the hydrogel core. Thirdly, the sheath material will be the source of ferrous gluconate for initial stage release. Since the sheath materials would be used to release ferrous gluconate in the initial stage and to delay and contain the release of this agent from the core, synthetic biodegradable biomaterials having good hydrophobicity and/or tight mesh structure were used. The core sheath design was expected and was indeed observed to provide sustained release of the incorporated spermiostatic agent over a desired period. By using a combination of a variety of core-sheath design concepts, such as multicore-sheath design, a wide range of release profiles could be generated and tailored accordingly to specific clinical needs. This can include variable terms of use, for example, for short term contraceptive usage for 3-7 days, or full-cycle (28 day) anti-viral, anti-SST and contraceptive protection.

The biodegradable hydrogel cores used in the third generation were three-dimensional hydrogel networks consisting of dextran-PLA (Park et al., "Biodegradable Hydrogels for Drug Delivery," Technomic (1993), which is hereby incorporated by reference in its entirety). Both dextran and PLA are FDA-approved biomaterials and hence would ensure biocompatibility, contain the cost of development, and bring the products to clinical trials at a faster pace. The technology of the present invention combines the merits of natural biodegradable polymers like dextran with synthetic biodegradable polymers like PLA into a single entity (via chemical crosslinking) so that there would be no phase separation, resulting in better and more predictable release of the incorporated biochemical agents. By controlling the composition ratio of dextran (as hydrophilic component) to PLA (as hydrophobic component), a wide range of swelling properties (i.e., a wide range of drug release profiles), differing degrees of hydrophobicity, and a three dimensional porous network having pore sizes between 0.1 .mu. and 600 .mu. can be achieved.

Five versions (A, B, C, D, and DA) of the third generation device were developed. They varied in the number and type of Sheath materials, concentration of the impregnated ferrous gluconate, and use of L-ascorbic acid. The same hydrogel core was used for all five versions. The compositions of samples A, B, C, D, and DA are as follows.

Sample A contained a core made of Dextran-Al hydrogel, with 2% ferrous gluconate by weight. The inner first sheath was made of the copolymer of .epsilon.-caprolactone and L-lactide containing ferrous gluconate (73.8% by weight of the polymer). The second sheath consisted of poly-.epsilon.-caprolactone containing predetermined amounts of ferrous gluconate.

Sample B had the same hydrogel core as Sample A with 2% ferrous gluconate by weight. The inner first layer contained poly-.epsilon.-caprolactone/poly-L-lactide copolymer containing predetermined amounts of ferrous gluconate. The second layer was poly-.epsilon.-caprolactone homopolymer containing predetermined amounts of ferrous gluconate. The third layer was made up of poly-.epsilon.-caprolactone/poly-L-lactide/polyethylene glycol copolymer, without ferrous gluconate.

Sample C had the same hydrogel core as Sample A containing 2% ferrous gluconate by weight. The inner first sheath was poly-.epsilon.-caprolactone/poly-L-lactide copolymer containing predetermined amounts of ferrous gluconate. The second inner sheath was of poly-.epsilon.-caprolactone-homopolymer containing predetermined amounts of ferrous gluconate.

Sample D had the same hydrogel core as Sample A containing 2% dihydrate ferrous gluconate by weight. This core material was coated by the following four layers of biodegradable polymers. The first layer was poly-D-L-lactide macromer impregnated with predetermined amounts of ferrous gluconate. The second layer was poly-.epsilon.-caprolactone/poly-L-lactide/polyethylene glycol copolymer containing predetermined amounts of ferrous gluconate. The third layer was poly-.epsilon.-caprolactone/pol-y-L-lactide copolymer impregnated with predetermined amounts of ferrous gluconate. The fourth layer also contained poly-.epsilon.-caprolactone/po-ly-L-lactide copolymer but was not impregnated with ferrous gluconate.

Figure 6:
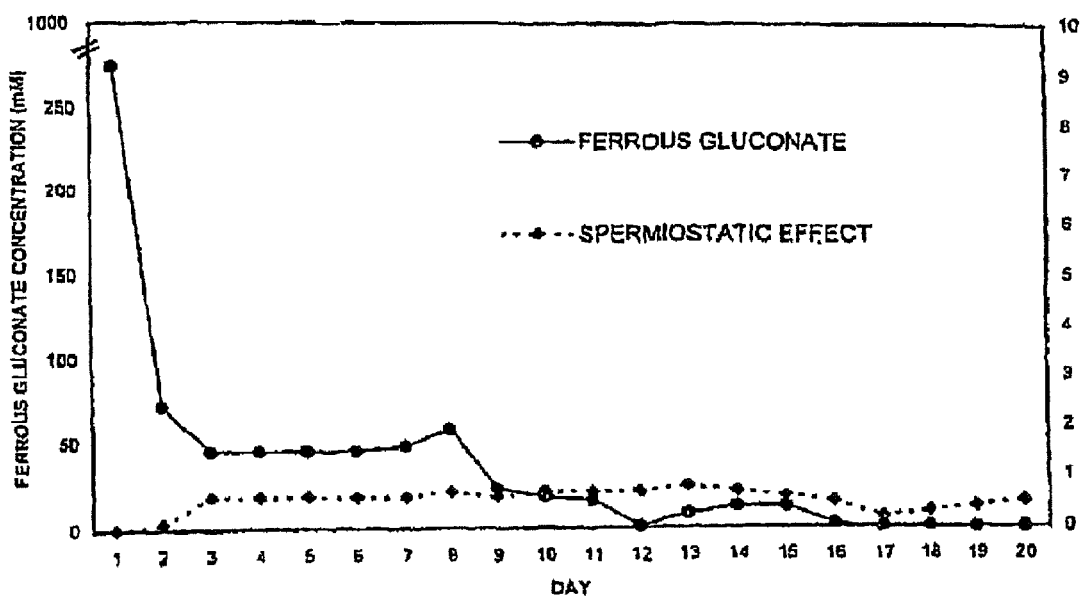
FIG. 6 shows the daily release of ferrous gluconate from matrix Sample B and the spermiostatic effect (in seconds) over a 20 day time course.

The ferrous gluconate release profiles from the first four of the third generation samples are shown in FIGS. 5-8. Sample A, shown in FIG. 5, and Sample B, shown in FIG. 6, showed efficacious spermiostatic activity for 8 days. Thus, these two samples are candidates for contraceptive devices of one-week duration; however, they are not sufficient for longer sustained release for the 28-day period.

Figure 7:
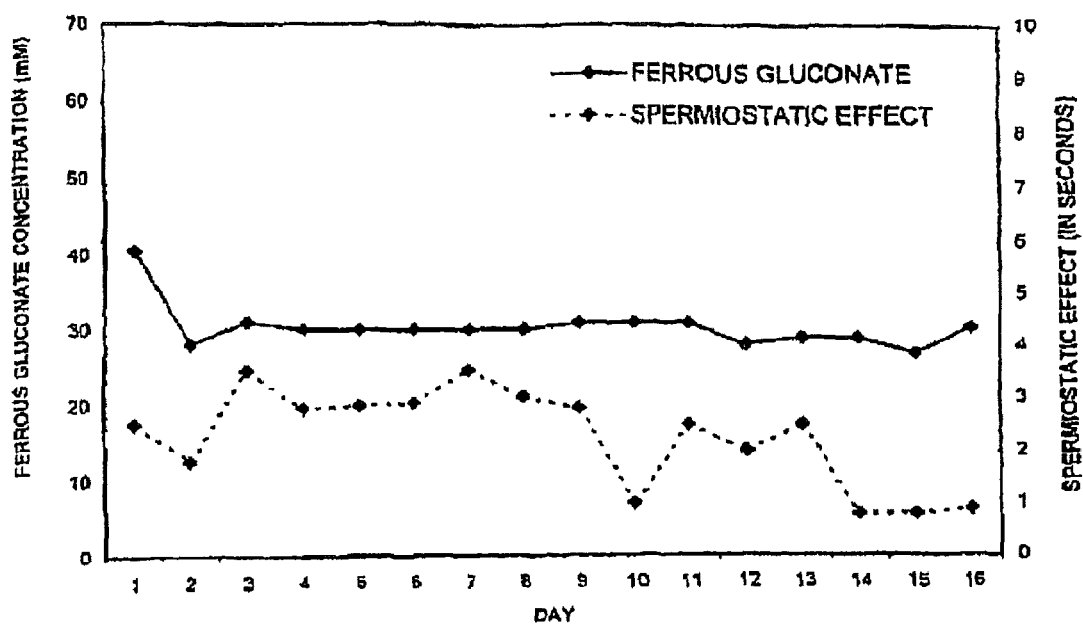
FIG. 7 shows the daily release of ferrous gluconate from matrix Sample C and the spermiostatic effect (in seconds) over a 16 day time course.
Figure 8:
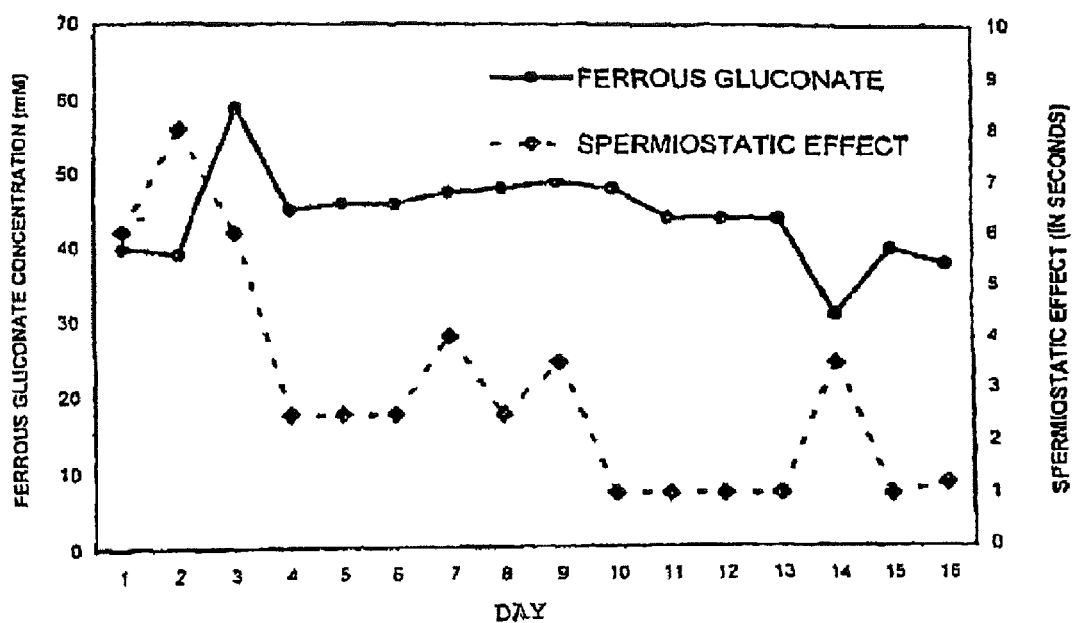
FIG. 8 shows the daily release of ferrous gluconate from matrix Sample D and the spermiostatic effect (in seconds) over a 16 day time course.

Sample C, shown in FIG. 7, and Sample D, shown in FIG. 8, exhibited acceptable daily release rates of ferrous gluconate and with approximately 33% and 42% biodegradability of the matrices, respectively, for a period of 16 days. Release rates are shown in Table 3 as a change in the weight of the respective matrix. However, Sample D showed the best sustained controlled release among all the three generations of matrices and appears to have the potential for delivering efficacious spermiostatic agents for longer periods than other matrices tested.

TABLE 3

| CHANGE IN THE WEIGHT OF THE MATRICES C AND D | | | | |
|---|---|---|---|---|
| Sample | Initial weight (gm) | Final Weight (gm) | Differences (gram) | Days |
| Sample C | 0.5541 (gm) | 0.375 (gm) | 0.179 (gm) | 16 |
| Sample D | 0.5406 (gm) | 0.306 (gm) | 0.234 (gm) | 16 |

Figure 9:
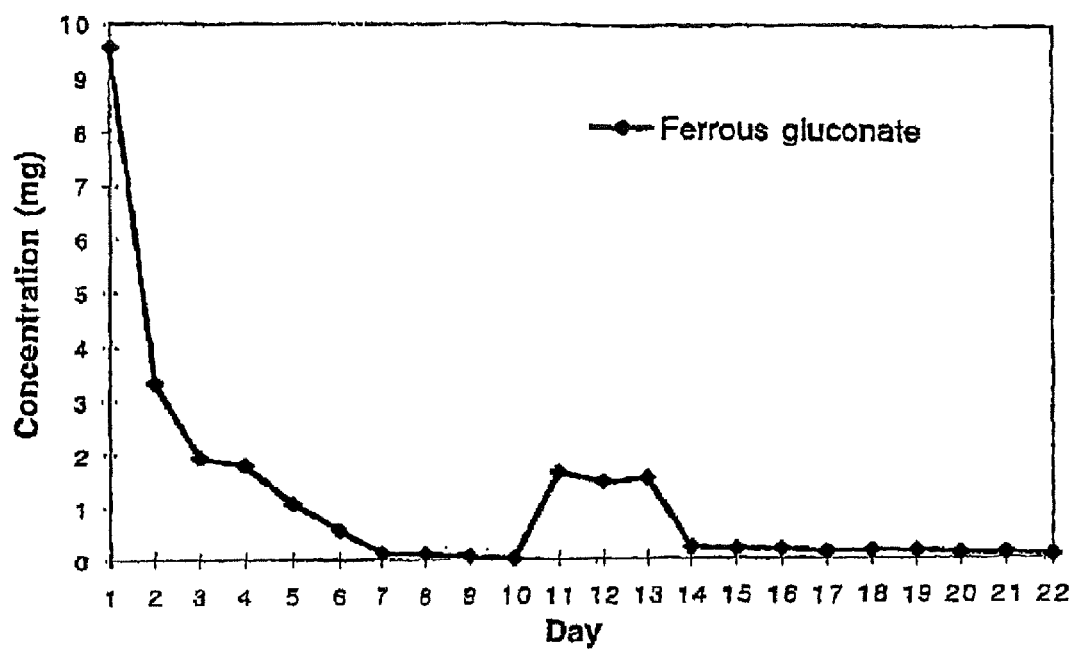
FIG. 9 shows the daily release of ferrous gluconate from hydrogel matrix Sample DA over a 22 day time course.
Figure 10:
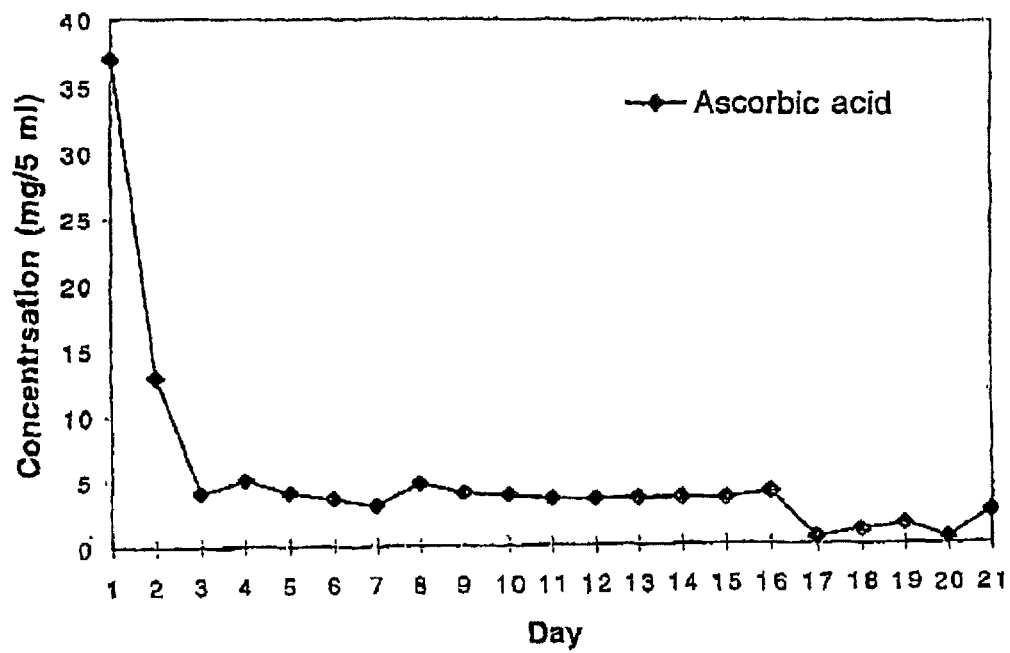
FIG. 10 shows the daily release of ascorbic acid from hydrogel matrix DA over a 21 day time course.
Figure 11:
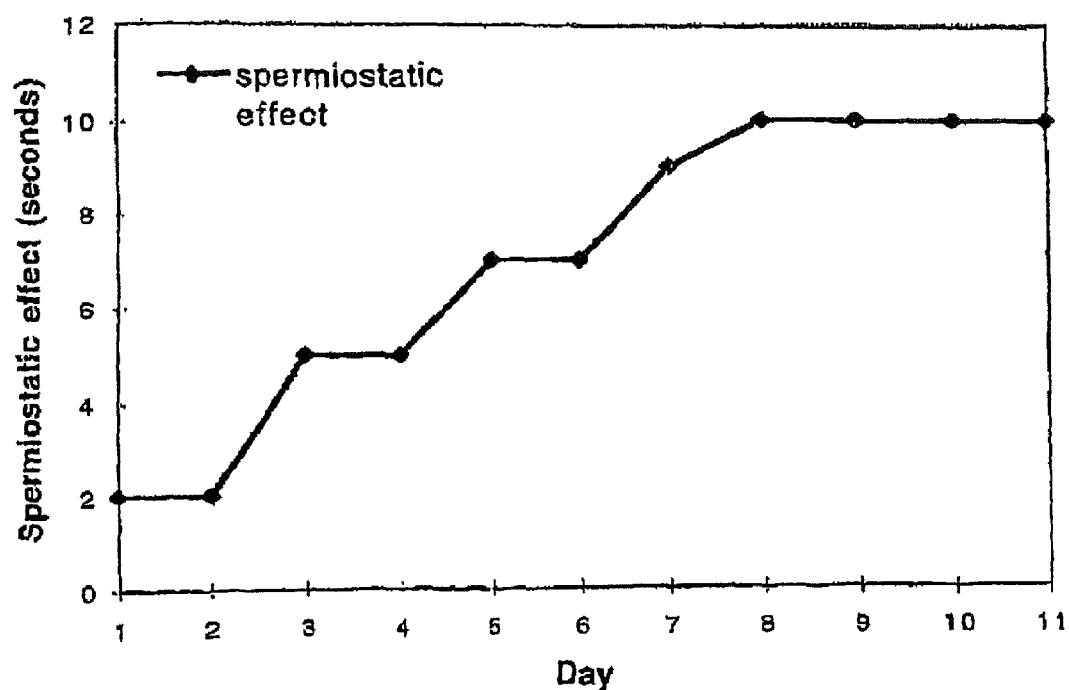
FIG. 11 shows the spermiostatic effect of the daily eluates of hydrogel matrix Sample DA over an 11 day time course.
Figure 12:
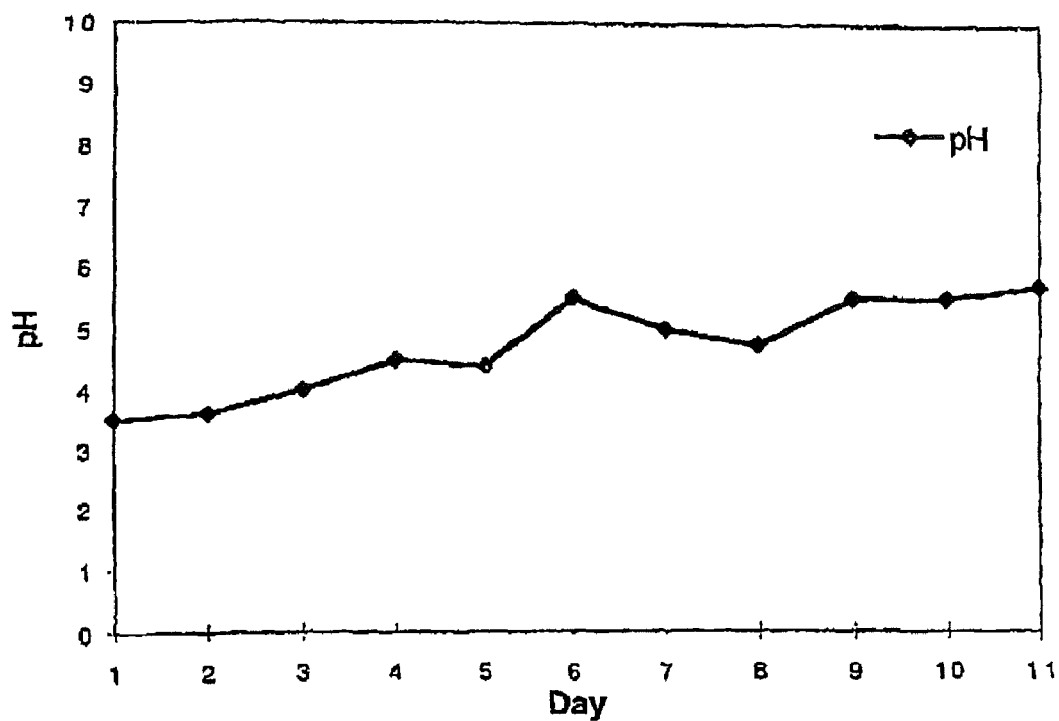
FIG. 12 shows the pH of the daily eluates of the hydrogel matrix Sample DA over an 11 day time course.

Sample DA contained the same hydrogel core as Sample D containing 2% ferrous gluconate by weight. In addition, the hydrogel core consisted of predetermined amounts of L-ascorbic acid, photoinitiator 2,2-dimethoxy-2-phenyl acetophenone, and N,N'-dimethyl formamide. The inner first layer was composed of poly-D-L-lactide macromer, ferrous gluconate, L-ascorbic acid, photoinitiator 2,2-dimethoxy-2-phenyl acetophenone, and NN'-dimethylformamide. The second inner sheath contained lactide/caprolactone/ethylene oxide copolymer and predetermined amounts of ferrous gluconate, L-ascorbic acid, and chloroform (6% by weight). The third layer was made up of lactide/caprolactone copolymer, ferrous gluconate, L-ascorbic acid, and chloroform, again 6% by weight. Sample DA was coloaded with both ferrous gluconate and ascorbic acid. The daily eluates from matrix DA were analyzed for ferrous gluconate and ascorbic acid as described earlier and shown in FIG. 9 and FIG. 10, respectively. The spermiostatic effect and effect on the increase in the viscosity of the cervical mucus is shown in Table 2. The spermiostatic activity was tested for 11 days and increase in the viscosity of the cervical mucus was tested for 15 days. As shown in FIG. 11, the spermiostatic effect was achieved within 10 seconds and the pH of eluates was stabilized between 5 and 6, as shown in FIG. 12. It is clearly indicated that a combination of iron and ascorbic acid has the potential of being an effective spermiostatic agent.

Example 4

Testing of Acidity of Acid-Rich Biodegradable Biomaterials

The objective of this example was to determine whether, in addition to being the vehicle for controlled delivery of spermiostatic agents, the acid-rich biodegradable biomaterials of the present invention could also serve as an acid donor to make the surrounding medium acidic for enhancing the spermiostatic activity. The numbers of the free —COOH groups could also be modified to provide the preferred acidic environment by changing the reaction conditions for augmenting the spermiostatic effect. In this preliminary study, a fixed amount of dextran-maleic acid hydrogel and a co-poly(ester amide) were separately immersed in distilled water and the pH of the water was measured for an extended period. Table 4 summarizes these findings.

TABLE 4

CHANGE OF pH OF AQUEOUS MEDIUM IN THE PRESENCE OF ACID-RICH BIODEGRADABLE BIOMATERIALS

| Immersion Time (Days) | Dextran-Maleic Acid pH | Co-Poly (ester-amide) pH |
|---|---|---|
| 0 | 6.20 | 6.28 |
| 1 | 4.33 | 5.31 |
| 3 | 4.39 | 4.41 |
| 8 | 4.42 | 4.31 |
| 15 | 5.20 | 4.17 |

These data illustrate that the biodegradable biomaterials of the present invention could be used not only as the hydrogel core and/or sheath materials for this proposal, but could also have the advantage of providing an adequate acidic environment for impeding sperm motility.

Example 5

In Vitro Rabbit Sperm Immobilization Studies

The spermiostatic effect of the elutes of hydrogel DA impregnated with ferrous gluconate and ascorbic acid on rabbit sperm in7 vitro was examined. Due to the necessity of using rabbit sperm on the same day that the ejaculates are collected, daily eluates from five consecutive days were analyzed. Rabbit semen was diluted three-fold with phosphate buffered saline to achieve counting efficiency of approximately $50.times.10.sup.6$ per ml. Twenty .mu.l of eluate was mixed with 20 .mu.l of the diluted semen. In Day 1 and Day 3 eluates with up to 1:3 dilution, all sperm were immobilized instantaneously with shaking movement. Day 4 eluates caused immobilization with shaking or shivering, but no movement. Day 5 eluates showed slower immobilization and increased number (up to 10%) of shaking or shivering sperm.

Example 6

Evaluation of the Effect of the Contraceptive Core-Sheath Matrices on Rabbit Sperm Function In Vivo On Day 1, female rabbits in estrus were selected using teaser males. The hydrogel impregnated with contraceptive core-sheath matrices corresponding to matrix sample DA, described above, was inserted into the anterior vagina within a wide insemination pipette at 11 AM. The estrus female was mated some 6 hours later to a male of known fertility (at about 5 PM) and then given 50 IU human chorionic gonadotrophin (hCG) intravenously via ear vein to ensure ovulation.

A functional population of spermatozoa sufficient to ensure fertilization was established within the rabbit cervix by 5 minutes after mating/ejaculation as described by Bedford, "The Rate of Sperm Passage Into the Cervix After Coitus in the Rabbit," J. Reprod.; Fertil. 25:211-218 (1971), which is hereby incorporated by reference in its entirety. However, for the purposes of this study a post-coital evaluation of the residual vaginal sperm population in females with the contraceptive gel was conducted approximately 30 minutes after ejaculation. This was accomplished by insertion of an artificial insemination pipette as far as the cervix, in the manner used for artificial insemination, and then aspiration of anterior vaginal content which was examined under phase microscope to determine the percentage and quality of sperm motility. All sperm appeared 100% immobilized.

On Day 2, the same female was again mated, and a post-coital examination of the vaginal content revealed 100% immobilized (dead) sperm. The pH of the vaginal canal after coitus was 5.0. No irritation of the vaginal tissue was detectable. Sperm retrieved from the vaginal canal were placed in modified human tubal fluid (Irvine Scientific, Santa Ana, Calif.) buffered with HEPES and incubated at 37.degree. C. for purposes of rejuvenation. No sperm were capable of being rejuvenated, indicating complete sperm immobilization was achieved by the contraceptive core-sheath matrix.

In rabbits, a pregnancy can be palpably detected at ten days, therefore from Day 11 of the study forward, the mated female was checked for pregnancy. Up to and including 21 days after the initial mating no pregnancy occurred, indicating the contraceptive efficacy of the matrix containing the sperm iostatic/spermicidal agents of the present invention.

Example 7

A Two-Hydrogel Core Device

In this design, there will be two hydrogel cores separated by several layers of biodegradable hydrophobic polymer sheath. The objective of the inner core is to facilitate the sustained release of the impregnated agents during the late stage of application. The outer core will be used to improve the release of the spermiostatic agents in the middle stage of application. The inner and outer cores can be made from either the same or different hydrogel precursors or from the same hydrogel precursors, but with different DS, i.e., different tightness of the three-dimensional network structure. A prolonged and more sustained release will require a tighter three dimensional network structure, i.e., higher DS. The insulating materials that separate the two cores will be the sheath materials described above. These sheath materials will have the spermiostatic agents impregnated at different concentrations. There will be several options for the number of sheath layers and their thickness. Fewer and/or thinner-sheath layers can be expected to accelerate the release of the incorporated spermiostatic agents.

Example 8

A Five-Hydrogel Core Device

In this design, the desirable release duration is divided into finer, more discrete periods, i.e., early, early-middle, middle, middle-late, and late stages. This discrete division of the release periods provides for the fine-tuning of the release profiles to permit even smoother and more sustained release of the spermiostatic, spermicidal and anti-infective agents incorporated into each hydrogel core. The innermost layer will be for the late stage release; the next innermost layer will be for the riddle-late stage and so on, with the outermost layer for the early stage release. These hydrogel cores will be separated by sheath materials in the same manner as the two-hydrogel core design.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

We claim:

1. An intravaginal contraceptive device, comprising:
   a biocompatible support structure, configured to be inserted into a woman's vagina;
   the support structure comprising a non-hormonal contraceptive composition, the support structure and composition adapted to provide sustained release of contraceptively effective amounts of the composition into the woman's vagina for three days;
   the contraceptive composition which is released for the three days, comprising:
      a sperm-mobility reducing effective amount of ferrous gluconate; or ferrous sulfate and combinations thereof;
      ascorbic acid in an effective amount to increase viscosity of cervical mucus; and
      a pH buffering effective amount of ampholines;
      the composition which is released for the three days formulated to maintain a vaginal pH at a spermiostatic level.

2. The device of claim 1, wherein the composition comprises ferrous gluconate.

3. The device of claim 1, wherein the ampholine component comprises poly-amino acids or polycarboxylic acids or combinations thereof.

4. The device of claim 3, wherein the composition comprises ferrous gluconate.

5. The device of claim 1, wherein the composition is effective to maintain the pH in the vaginal cavity at about 5.

6. The device of claim 1, wherein the composition comprises magnesium chloride or calcium chloride.

7. The device of claim 1, wherein the support structure comprises poly-DL lactide.

8. The device of claim 1, wherein the support structure comprises hydrogel material.

9. The device of claim 1, wherein the ampholine component comprises an acid-rich polymer.

10. The device of claim 1, wherein the support structure has an annular shape.

11. The device of claim 1, wherein the composition is formulated to prevent the pH in a vagina from increasing in the presence of semenal fluid.

12. An intravaginal contraceptive device, comprising:
    a biocompatible support structure, configured to be inserted into a woman's vagina;
    the support structure comprising a non-hormonal contraceptive composition, the support structure and composition adapted to provide sustained release of contraceptively effective amounts of the composition into the woman's vagina for seven days;
    the contraceptive composition which is released for the seven days, comprising:
       a sperm-mobility reducing effective amount of ferrous gluconate or ferrous sulfate and combinations thereof;
       ascorbic acid in an effective amount to increase the viscosity of cervical mucus; and
       a pH buffering effective amount of ampholines;
       the composition which is released for the seven days formulated to maintain a vaginal pH at a spermiostatic level.

13. An intravaginal contraceptive device, comprising:
    a biocompatible support structure, configured to be inserted into a woman's vagina;
    the support structure comprising a non-hormonal contraceptive composition, the support structure and composition adapted to provide sustained release of contraceptively effective amounts of the composition into the woman's vagina for 16 days;
    the contraceptive composition which is released for the 16 days, comprising:
       a sperm-mobility reducing effective amount of ferrous gluconate or ferrous sulfate and combinations thereof;
       ascorbic acid in an effective amount to increase the viscosity of cervical mucus; and
       a pH buffering effective amount of ampholines;
    the composition which is released for the 16 days formulated to maintain a vaginal pH at a spermiostatic level.

14. An intravaginal contraceptive device, comprising:
    a biocompatible support structure, configured to be inserted into a woman's vagina;
    the support structure comprising a non-hormonal contraceptive composition, the support structure and composition adapted to provide sustained release of contraceptively effective amounts of the composition into the woman's vagina for 28 days;
    the contraceptive composition which is released for the 28 days, comprising:
       a sperm-mobility reducing effective amount of ferrous gluconate or ferrous sulfate and combinations thereof;
       ascorbic acid in an effective amount to increase the viscosity of cervical mucus; and
       a pH buffering effective amount of ampholines;
    the composition which is released for the 28 days formulated to maintain a vaginal pH at a spermiostatic level.

15. The device of claim 1, wherein the device comprises effective amounts of material to maintain a pH of about 5-6 in a vagina during the sustained release of said composition, in the presence of seminal fluid.

16. The device of claim 14, wherein the composition comprises ferrous gluconate.

17. The device of claim 16, including poly-amino acids, polycarboxylic acids or combinations thereof.

* * * * *